(12) United States Patent
Wihlborg et al.

(10) Patent No.: US 6,906,796 B2
(45) Date of Patent: Jun. 14, 2005

(54) DEVICE AND METHOD FOR IRRADIATION

(75) Inventors: Nils Wihlborg, Helsingborg (SE); Göran Persson, Jonstorp (SE); Erland Leide, Helsingborg (SE)

(73) Assignee: Foss Analytical AB, Hoganas (SE)

( * ) Notice: Subject to any disclaimer, the term of this patent is extended or adjusted under 35 U.S.C. 154(b) by 333 days.

(21) Appl. No.: 10/222,985

(22) Filed: Aug. 19, 2002

(65) Prior Publication Data

US 2003/0172452 A1 Sep. 18, 2003

(30) Foreign Application Priority Data

Aug. 17, 2001 (SE) ............................................... 0102745

(51) Int. Cl.[7] ............................................... G01N 21/01
(52) U.S. Cl. ................. 356/244; 356/239.1; 250/223 R
(58) Field of Search ......................... 356/244, 335–343, 356/239.1, 239.8; 250/288, 339.11, 339.12, 223 R; 209/588

(56) References Cited

U.S. PATENT DOCUMENTS

| | | | | |
|---|---|---|---|---|
| 3,871,774 | A | * 3/1975 | Murata | ........................ 356/432 |
| 4,572,666 | A | * 2/1986 | Satake | ...................... 356/239.1 |
| 5,818,045 | A | * 10/1998 | Mark et al. | ............. 250/339.12 |
| 6,100,973 | A | 8/2000 | Lawandy | |
| 6,495,825 | B1 | * 12/2002 | Chace et al. | ................. 250/288 |
| 6,556,295 | B2 | * 4/2003 | Leide et al. | ................. 356/244 |

FOREIGN PATENT DOCUMENTS

| | | | |
|---|---|---|---|
| DE | 196 30 005 A1 | 1/1998 | |
| EP | 1 046 902 A2 | 10/2000 | |
| JP | 63-132141 | 4/1988 | |
| JP | 01161136 A | * 6/1989 | .......... G01N/21/85 |
| JP | 09257712 A | * 10/1997 | .......... G01N/21/85 |
| JP | 9-292344 | 11/1997 | |

OTHER PUBLICATIONS

Patent Abstracts of Japan :"Shell Cracked Grain Detecting Device" Publication No.: 57–172249, Publication Date: Oct. 23, 1982, Inventor: Satake Toshihiko.

Patent Abstract of Japan "Quality Decision Device for Hulled Rice" Publication No.: 01–161136, Publication Date: Jun. 23, 1989, Inventor: Kawanaka Michio.

* cited by examiner

*Primary Examiner*—Zandra V. Smith
*Assistant Examiner*—Sang H. Nguyen
(74) *Attorney, Agent, or Firm*—Browdy and Neimark, P.L.L.C.

(57) ABSTRACT

A device for irradiation of small particles, such as grains from cereals and like crops, for analysis of the quality of the particles, comprises a sample-feeding carrier (30), which has sample holders and is adapted to take up particle samples (2), which each comprise at least one particle, in the sample holders and transport the particle samples (2) to a place for irradiation (34). The device further comprises a radiating device (36) emitting electromagnetic radiation for irradiation of the particle samples (2), and radiation guides (22). The radiation guides (22) are attached on the sample-feeding carrier (30) for guiding the radiation emitted by the radiating device (36) to a particle sample (2) in a sample holder, when the particle sample (2) has been fed to the place for irradiation (34).

10 Claims, 3 Drawing Sheets

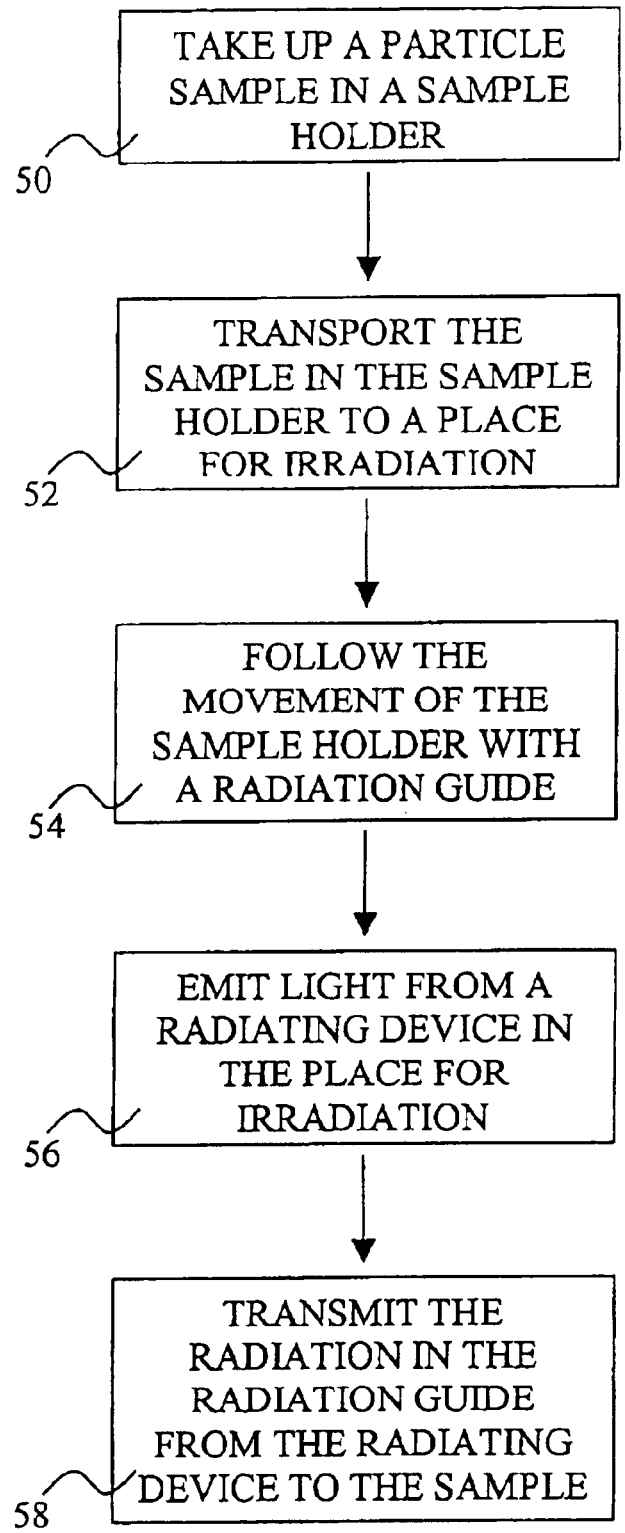

DEVICE AND METHOD FOR IRRADIATION

FIELD OF THE INVENTION

The present invention relates to a device and a method for irradiation of small particles, such as grains from cereals and like crops, for analysis of the quality of the particles.

BACKGROUND ART

Inspection of different kinds of cereals and other crops is today made all over the world to determine the quality of the cereals in commercial transactions and handling. The inspection aims at examining a selected representative sample from a large consignment and determining the presence of non-desirable grains and particles. The non-approved grains and particles are classified and the quantity of each class is determined. Owing to the distribution of the various grains, the sample and, thus, the consignment will be given a grading, which is a decisive factor in connection with payment and handling of the consignment.

It is desirable that the classification be made by means of some kind of automated process. The analyses performed on these samples are often based on the sample material being irradiated by some kind of light. The sample is then analyzed by means of, for example, spectroscopic measurements, measurements on fluorescent light or image analysis. An analysis instrument for such measurements may comprise a mechanism, which positions sample material in a suitable place for irradiation by one or more light sources, and one or more sensors that measure the light that has interacted with the sample material.

In order to establish a reliable result from the analysis, measurements should be performed on several different and separate objects. This could be achieved in three different ways. The first alternative is to advance a new measurement object in front of the sensor for each part of the measurement. The second alternative is to move the sensor to a new measurement object for each part of the measurement and the third alternative is to measure several objects in one recording.

Due to measuring difficulties and handling reasons, the first alternative is normally preferable. The sensor is normally connected to analysis equipment for analysis of measurement results, and to a power supply. This makes movement of the sensor according to the second alternative complicated and undesirable. If several objects are measured in one recording according to the third alternative, it is often difficult to record variations among the objects. Further, certain set-ups for the irradiation are impossible to achieve for this alternative.

The first alternative requires some kind of sample-feeding mechanism, where the measurement object is placed in a sample holder, which is then advanced to a correct measurement position for the analysis. In order to speed up the sample feeding, several sample holders are often used, so that the placement of the sample in the sample holder, the measurement of the sample and the removal of the sample from the sample holder could be performed simultaneously in different positions.

It is often important that the samples be irradiated in a specific way. It is desired that a fixed light source be arranged at the measurement position, but for some irradiation arrangements this could be difficult to achieve. For example, in certain types of analyses, each particle is irradiated from a side of the particle, i.e. using radiation having a large angle of incidence in relation to a measuring direction from the particle towards a sensor. Such an analysis is preferable when determining the existence of cracks in rice grains. Irradiation from a side of the particle could also be of interest, when shadows are to be removed in different types of image analysis.

For such irradiation arrangements, radiation sources could be arranged to follow the feeding of the particle samples in order to irradiate the samples properly. However, this implies that a radiation source has to be arranged in connection to each sample holder. These radiation sources could have varying characteristics, which will affect the measurements and deteriorate the reliability of the measurements. Further, power supply has to be provided to a moving radiation source, which makes the arrangement complicated.

SUMMARY OF THE INVENTION

It is an object of the invention to solve the problems with sample irradiation described above. It is a further object of the invention to provide an easy way of irradiating moving particle samples.

The objects of the invention are achieved by a device for irradiation of small particles, such as grains from cereals and like crops, for analysis of the quality of the particles. The device comprises a sample-feeding carrier, which has sample holders and is adapted to take up particle samples, which each comprise at least one particle, in the sample holders and transport the particle samples to a place for irradiation. The device further comprises a radiating device emitting electromagnetic radiation for irradiation of the particle samples, and radiation guides. The radiation guides are attached on the sample-feeding carrier for guiding the radiation emitted by the radiating device to a particle sample in a sample holder, when the particle sample has been fed to the place for irradiation.

The objects of the invention are also achieved by a sample-feeding carrier for transporting small particles to a place for analysis of the quality of the particles. The carrier comprises sample holders, which are adapted to take up particle samples, which each comprise at least one particle, and radiation guides, which each comprise an outlet arranged close to a sample holder, thus enabling guiding of electromagnetic radiation to a particle sample in a sample holder.

The objects of the invention are further achieved by a method for irradiation of small particles for analysis of the quality of the particles. The method comprises the steps of feeding a particle sample, which comprises at least one particle, to a place for irradiation, and emitting electromagnetic radiation from a radiating device for irradiation of the particle samples. The method further comprises the step of guiding the radiation in a radiation guide, which follows the feeding of the particle sample, from the radiating device to the particle sample, when the particle sample is in the place for irradiation.

The invention allows a radiating device to be arranged on a fixed part of the device. Thus, an electric construction connected to the radiating device will need no movable parts. The irradiation of the particle samples is obtained through the guiding of the radiation in the radiation guides. Since the radiation guides are attached on the sample-feeding carrier, they will follow the movement of the carrier and the feeding of the particle samples. Thus, the radiation guides could be arranged to guide radiation to areas of the samples that otherwise would be hard to reach because of the movement of the samples. This also implies that radiation could be led to spots where provision of a radiation source is difficult. Further, the same radiation source will be used for the same measurement for each particle sample. As a result, a stability of the measurement could be ensured and problems with varying characteristics of different radiation sources for different sample holders are avoided.

The radiation guides could also be used for guiding radiation from different radiation sources to one sample during the feeding of the sample, and thus several irradiations of a particle sample by radiation sources with different radiation characteristics could easily be performed. Thus, several measurements could be performed on the same sample.

In the context of this invention, a radiation guide is defined as a device of a material that is transparent to the radiation of the wavelength emitted by the radiating device, the radiation guide forming a channel for transporting the radiation from a first to a second position with very small or no attenuation of the radiation during the transport.

Preferably, each sample holder has a shape corresponding to that of a particle for controlling the orientation of the particle in the sample holder. This is of special interest when analyzing rice kernels, since cracks in the rice kernels usually occur across the kernel. If the orientation of the particle or kernel is controlled, the cracks could more easily be detected, since the direction in which cracks should be found is known.

According to a preferred embodiment, each sample holder is elongate and has a short side, and a corresponding radiation guide is guiding the radiation emitted by the radiating device towards the short side of the sample holder, so that the radiation incides towards a short side of a particle in the sample holder. This is of further interest for rice kernels, since cracks in the rice kernels could be detected by irradiation from the sides of the kernels. This arrangement could also be used for eliminating shadows in a particle sample. Shadows are typically formed when irradiating an object from above. These shadows could erase contours of close objects and could therefore be misinterpreted by a detector. Thus, an erroneous measurement result could be returned if shadows are present.

Preferably, each radiation guide has an outlet, which is arranged in such relation to the sample holder so that radiation emitted from the outlet will irradiate a particle in the sample holder with sweeping incidence. If a particle is irradiated by radiation of sweeping incidence, i.e. if the radiation is directed to the particle with a large angle of incidence, most of the directly reflected radiation will not reach the detector. Thus, the diffusely reflected radiation will constitute a very large part of the detected radiation, providing information about the quality of the particle. Further, if a crack exists in the particle, the radiation will not be transmitted in the particle across the crack, which means that a crack will be easily detected.

According to another preferred embodiment, each radiation guide has an inlet, which is adapted to pick up radiation from the radiating device, said inlet extending along a direction of transport of the carrier. This implies that the radiation guide could collect radiation from the radiation source during movement. The radiation guide collects radiation that enters through the inlet and transports the collected radiation to the outlet without the output radiation being affected by the place of collection of the radiation. Since the inlet extends along a direction of transport of the carrier, the radiation guide will give a constant radiation amount to the particle sample during a movement of the inlet past the radiating device. Thus, the particle sample could be irradiated for a period of time, without need of stopping the transport of the particle sample in the place for irradiation. When measurement of the sample is performed on a moving sample, the measurements are speeded up considerably.

Preferably, the radiating device comprises two light sources, which are adapted to emit light in different wavelength ranges. This implies that the particle samples could be irradiated with different wavelengths for obtaining more information about the quality of the samples.

Preferably, the light sources are adapted to emit red and blue light, respectively. This could be used for simultaneous detection of different irradiations, since a conventional CCD camera records red and blue light in different channels.

According to yet another preferred embodiment, each radiation guide comprises a first and a second outlet for guiding the light. The first outlet is arranged at a first sample holder and the second outlet is arranged at a second sample holder adjacent to the first sample holder. Thus, the radiation guide could guide light to adjacent sample holders and a sample could be irradiated by radiation emanating from different directions from two adjacent radiation guides. This implies that a particle sample could simultaneously be irradiated by red light from one side and by blue light from the opposite side. The detection in different channels could then be enhanced by comparing the images of the particle under red irradiation and the particle under blue irradiation for easier detection of cracks.

Preferably, the radiation guides extend in the same plane as the carrier. This makes the device compact and easy to handle.

BRIEF DESCRIPTION OF THE DRAWINGS

The invention will now be described in more detail with reference to the accompanying drawings, which by way of example show a preferred embodiment of the invention.

FIG. 4 is a flow chart of a method according to the invention.

DETAILED DESCRIPTION OF A PRESENTLY PREFERRED EMBODIMENT

Figure 1:
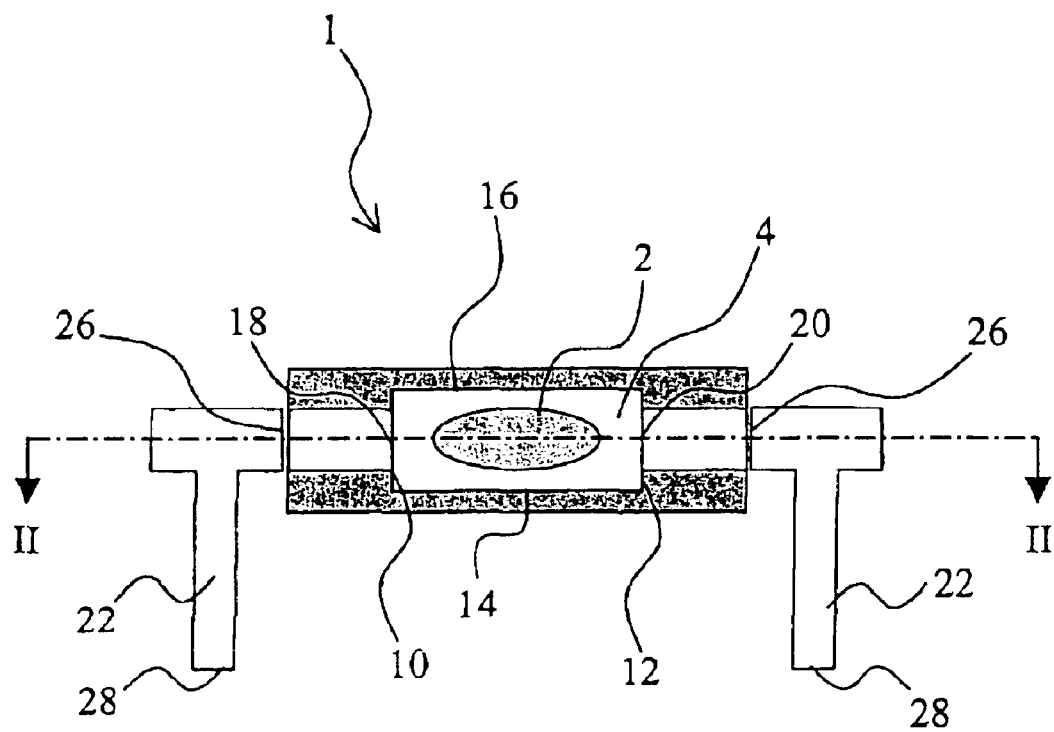
FIG. 1 is a schematic top view of a sample holder according to the invention.
Figure 2:
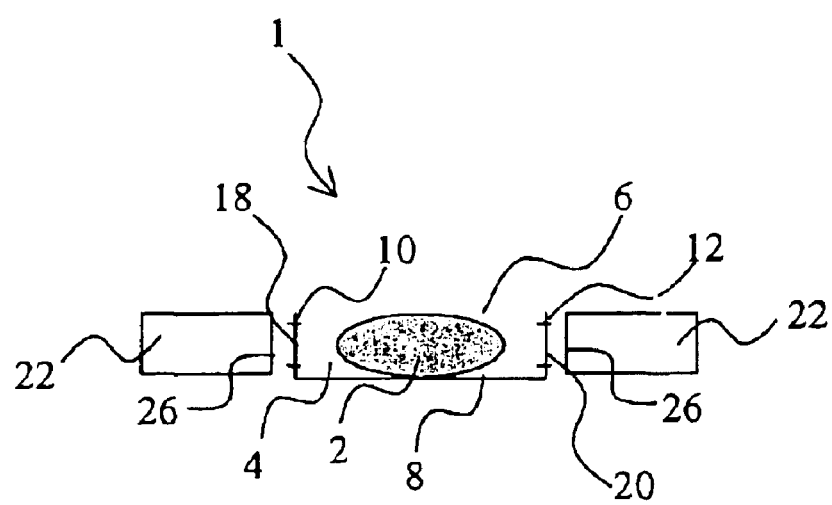
FIG. 2 is a sectional view along II—II of the sample holder in FIG. 1.

In FIGS. 1 and 2 a sample holder 1 for transporting a particle sample 2 is shown. The particle sample 2 comprises one kernel of an agricultural product that is to be analyzed. The sample holder 1 forms a cavity 4, into which a particle sample 2 falls. The cavity 4 is essentially formed like a particle for controlling the orientation of the particle. Thus, a particle that falls into the cavity 4 of the sample holder 1 is oriented in a specified way. This could be used in the analysis of the particle for easily obtaining information about the quality of the particle.

The cavity 4 of the sample holder 1 has an upper opening 6 through which the particles can fall into the cavity 4. The cavity 4 further has a bottom 8 for carrying the particle sample 2 and side walls 10, 12, 14, 16 restricting the movements and the orientation of the sample 2 in the cavity 4. In order to control the orientation of an elongate particle, the cavity 4 has two short side walls 10, 12 and two long side walls 14, 16. In each short side wall 10, 12 of the cavity 4, a hole 18, 20 is arranged for allowing radiation to reach the particle from the side of the particle.

Two radiation guides 22 are arranged by the holes 18, 20 in the sample holder 1. The radiation guides 22 are arranged so that an outlet 26 of the radiation guides 22 will let out light towards the hole 18, 20 and the particle sample 2 in the sample holder 1. The radiation guide 22 will thus enable a radiation source to be arranged in a suitable position considering the movements of the sample holders 1 and the general construction of the device. The form of the radiation guide 2 is very flexible. Therefore, it could be designed so that an inlet 28 of the radiation guide 22 will take up radiation from the suitably placed radiation source, when the radiation guide 22 passes the radiation source, and transmit the radiation from the radiation source to the particle sample 2.

In the particular application when cracks in rice kernels are to be detected, it is desired to irradiate a kernel or particle from its short side. In the above, a description is made of a device suited for this application. However, as will be understood by a person skilled in the art, any arrangement of the sample holders 1 is possible and the radiation guides 22 could be formed to transmit radiation to the particle sample 2 accordingly. Also, particles of any shape may be analysed.

Figure 3:
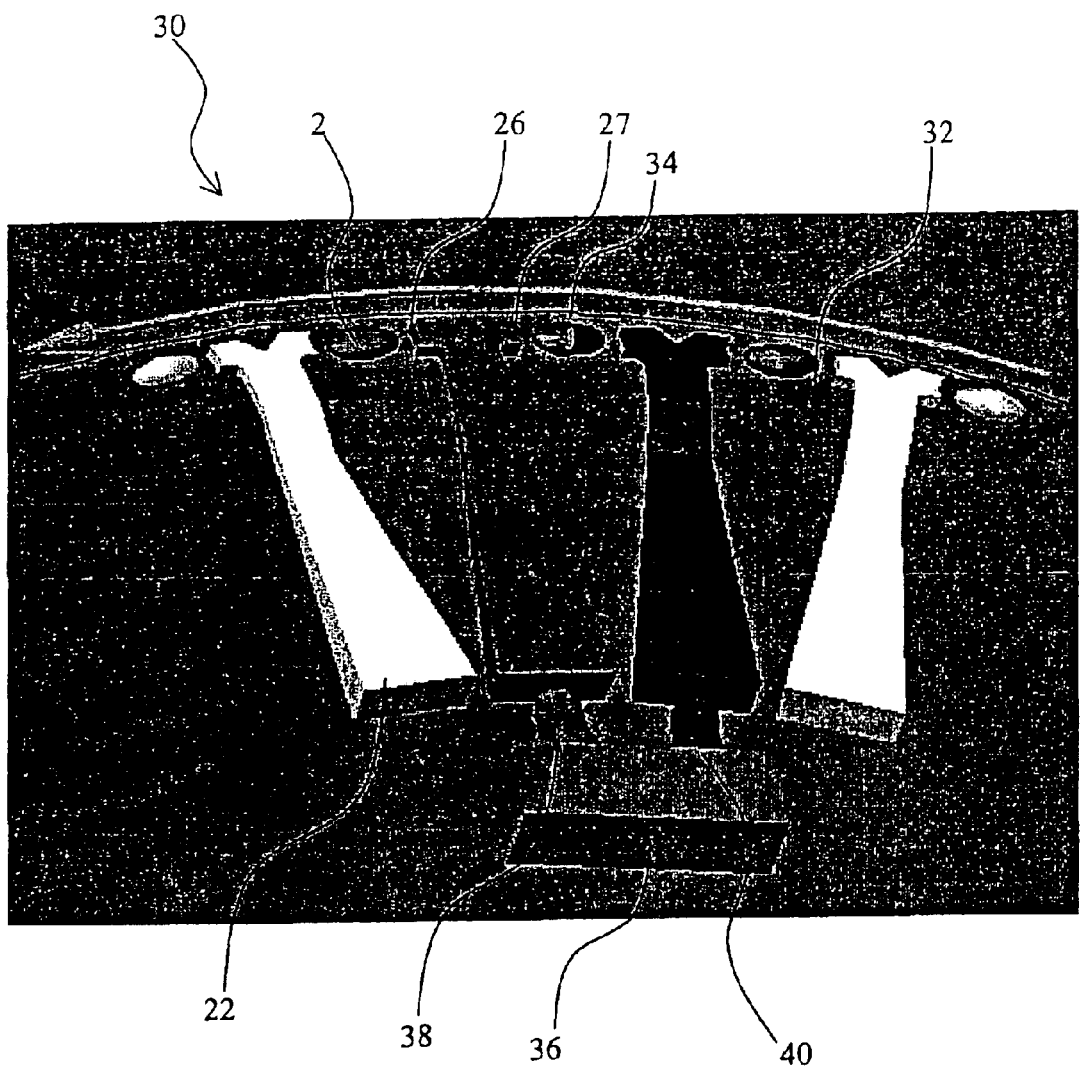
FIG. 3 is a perspective view of a device according to the invention.

In FIG. 3 a sample-feeding carrier 30 is shown. The sample-feeding carrier 30 comprises a rotatable disc 32. Cavities 4 for forming sample holders 1 are arranged at the peripheral edge of the disc 32. The disc 32 rotates for feeding the samples 2. In a first position (not shown) of the rotation, the disc 32 picks up samples 2, in a second position 34, the samples 2 are irradiated for analysis and in a third position (not shown), the sample holders 1 are emptied.

A radiating device 36 for irradiation of the product samples 2 is arranged in a fixed part of the device. A sample holder 1 on the disc 32 passes the radiating device 36 in the second position 34 for being irradiated by the radiating device 36. The radiating device 36 comprises two light sources 38, 40 emitting red and blue light, respectively.

Between two adjacent sample holders 1, a radiation guide 22 is arranged. The radiation guide 22 has two outlets 26, 27 for letting out radiation to both sample holders 1 on each side of the radiation guide 22. Thus, the same radiation guide 22 could be used for irradiation by red light of one sample holder 1 and irradiation by blue light of the adjacent sample holder 1. The inlet 28 of the radiation guide 22 extends along the direction of movement of the disk 32. Thus, the radiation guide 22 will take up radiation from the radiating device 36 over a distance as the radiation guide 22 passes the radiating device 36. This implies that the sample 2 will be irradiated during a period of time while passing the radiating device 36.

Referring to FIG. 4, a method according to the invention will now be described. First, a particle sample is acquired in a sample holder, step 50. Then, the sample is transported to a place for irradiation, step 52, by means of a sample-feeding carrier on which the sample holder is arranged. A radiation guide is attached to the sample-feeding carrier in connection with the sample holder. The radiation guide will therefore follow the movement of the sample holder, step 54. In the place for irradiation, a radiating device is arranged. The radiating device emits radiation for irradiating the sample, step 56. When the sample has been transported to the place for irradiation, the radiation guide will receive radiation from the radiating device. Then, the radiation guide transmits the radiation to the sample holder for irradiation of the particle sample, step 58.

It should be emphasized that the embodiments described herein are in no way limiting and that many alternative embodiments are possible within the scope of protection defined by the appended claims. For example, the radiation guides could be arranged in any manner relative to the sample holders depending on the desired irradiation set-up. Alternatively, optical fibers could be used as radiation guides.

The radiating device could be any device which can emit desired electromagnetic radiation. Thus, the radiating device could be a LED (Light Emitting Diode) or any other kind of lamp.

What is claimed is:

1. A device for irradiation of small particles for analysis of the quality of the particles, which comprises a sample-feeding carrier, which has sample holders and is adapted to take up particle samples, which each comprise at least one particle, in the sample holders and transport the particle samples to a place for irradiation, a radiating device emitting electromagnetic radiation for irradiation of the particle samples, and radiation guides, which are attached on the sample-feeding carrier for guiding the radiation emitted by the radiating device to a particle sample in a sample holder, when the particle sample has been fed to the place for irradiation wherein at least one radiation guide comprises a first and a second outlet for directing the radiation out of the radiation guide, said first outlet being arranged at a first sample holder and said second outlet being arranged at a second sample holder adjacent to the first sample holder.

2. The device according to claim 1, wherein each sample holder has a shape corresponding to that of a particle for controlling the orientation of the particle in the sample holder.

3. The device according to claim 2, wherein each sample holder is elongate and has a short side, and a corresponding radiation guide guides the radiation emitted by the radiating device towards the short side of the sample holder, so that the radiation is incident towards a short side of a particle in the sample holder.

4. The device according to claim 1, wherein the first and second outlet of the at least one radiation guide are arranged in such relation to the sample holder, respectively, so that radiation emitted from the first and second outlet will irradiate a particle in the first and second sample holder, respectively, with sweeping incidence.

5. The device according to claim 1, wherein each radiation guide has an inlet, which is adapted to pick up radiation from the radiating device, said inlet extending along a direction of transport of the carrier.

6. The device according to claim 1, wherein the radiating device comprises two light sources, which are adapted to emit light in different wavelength ranges.

7. The device according to claim 6, wherein the light sources are adapted to emit red and blue light, respectively.

8. The device according to claim 1, wherein the radiation guides extend in the same plane as the carrier.

9. A sample-feeding carrier for transporting small particles to a place for analysis of the quality of the particles, which comprises sample holders, which are adapted to take up particle samples, which each comprise at least one particle, and radiation guides for guiding electromagnetic radiation to a particle sample in a sample holder, wherein at least one radiation guide comprises a first and second outlet for directing the radiation out of the radiation guide, said first outlet being arranged at a first sample holder, and said second outlet being arranged at a second sample holder adjacent to the first sample holder.

10. A method for irradiation of small particles, for analysis of the quality of the particles, which comprises the steps of:

feeding a particle sample, which comprises at least one particle, to a place for irradiation, emitting electromagnetic radiation from a radiating device for irradiation of the particle samples, guiding the radiation in a radiation guide, which follows the feeding of the particle sample, from the radiating device to the particle sample, when the particle sample is in the place for irradiation, and using the same radiation guide for directing the radiation towards two separate adjacent sample holders by the radiation guide emitting radiation in two different directions.

* * * * *